(12) United States Patent
Ayala et al.

(10) Patent No.: US 8,802,653 B2
(45) Date of Patent: Aug. 12, 2014

(54) DEODORANT COMPOSITIONS

(75) Inventors: Nelson Ayala, Lynchburg, VA (US); Ruby Anderson, Rustburg, VA (US)

(73) Assignee: C.B. Fleet Company, Inc., Lynchburg, VA (US)

( * ) Notice: Subject to any disclaimer, the term of this patent is extended or adjusted under 35 U.S.C. 154(b) by 0 days.

(21) Appl. No.: 13/240,416

(22) Filed: Sep. 22, 2011

(65) Prior Publication Data

US 2012/0083467 A1  Apr. 5, 2012

Related U.S. Application Data

(60) Provisional application No. 61/389,132, filed on Oct. 1, 2010.

(51) Int. Cl.
| | |
|---|---|
| *A61K 31/724* | (2006.01) |
| *A61K 31/717* | (2006.01) |
| *A61K 31/715* | (2006.01) |
| *A61Q 15/00* | (2006.01) |

(52) U.S. Cl.
USPC .................. 514/58; 514/54; 514/57; 536/103; 536/56

(58) Field of Classification Search
USPC ........................... 514/58, 54, 57; 536/103, 56
See application file for complete search history.

(56) References Cited

U.S. PATENT DOCUMENTS

| | | | |
|---|---|---|---|
| 4,010,253 | A | 3/1977 | Reese et al. |
| 4,565,693 | A | 1/1986 | Marschner |
| 4,606,912 | A | 8/1986 | Rudy et al. |
| 4,675,177 | A | 6/1987 | Geary |
| 5,643,559 | A | 7/1997 | Eigen et al. |
| 5,770,185 | A | 6/1998 | Wachter et al. |
| 5,968,488 | A | 10/1999 | Wachter et al. |
| 6,277,359 | B1 | 8/2001 | Raths et al. |
| 8,685,380 | B2 | 4/2014 | Ayala |
| 2004/0033984 | A1 * | 2/2004 | Muller ............................ 514/58 |
| 2006/0057090 | A1 | 3/2006 | Buchwald-Werner |
| 2007/0281047 | A1 | 12/2007 | Henry et al. |
| 2008/0008727 | A1 * | 1/2008 | Fredon et al. ................. 424/401 |
| 2008/0138850 | A1 | 6/2008 | Vielhaber et al. |
| 2009/0068255 | A1 | 3/2009 | Yu et al. |
| 2009/0220444 | A1 | 9/2009 | Teckenbrock et al. |
| 2012/0100095 | A1 | 4/2012 | Ayala |

FOREIGN PATENT DOCUMENTS

| | | |
|---|---|---|
| WO | 91/07165 | 5/1991 |

OTHER PUBLICATIONS

Boonme, P. et al., "Antiperspirants and deodorants: Active ingredients and novel formulations", Journal of Clinical Dermatology, Review Article, vol. 1, issue 2, pp. 67-72, (2010).
Alvinwriter, "Why Choose pH-Balanced Deodorants", Article Alley, http://alvinwriter.articlealley.com/why-choose-phbalanced-deodorants-573497.html, p. 1, (2008).
McKetta Jr, J., "Low pH Shampoos", Encyclopedia of Chemical Processing and Design, vol. 12, pp. 110-111, (1981).
"Sodium Cocoyl Hydrolyzed Wheat Protein", EWG's Skin Deep® Cosmetics Database, found at www.ewg.org/skindeep/ingredient/706047/SODIUM_COCOYL_HYDROLYZED_WHEAT_PROTEIN/, printed on Sep. 10, 2012.
"Zinc Glycinate", EWG's Skin Deep® Cosmetics Database, found at www.ewg.org/skindeep/ingredient/724924/ZINC_GLYCINATE/, printed on Sep. 10, 2012.
"Sodium Laureth Sulfate", EWG's Skin Deep® Cosmetics Database, found at www.ewg.org/skindeep/ingredient/706089/SODIUM_LAURETH_SULFATE/, printed on Sep. 10, 2012.
"Polysorbate 20", CosmeticsINFO.org, found at www.cosmeticsinfo.org/ingredient_details.php?ingredient_id=454, printed on Sep. 17, 2012.
Neolone Bactericide for Personal Care Products, "Neolone™ MxP Preservative", www.rhpersonalcare.com/neoloneMxP.html, pp. 1-2, printed on Jul. 1, 2009.
Product Description, Neolone™ MXP, www.dow.com/products/market/personal-care-and-apparel/product-line/neolone-for-personal-care/product/neolone-mxp/, 1 page, printed on Jul. 1, 2009.
Product Description and directions, Summer's Eve Feminine Deodorant Spray, Baby Powder, www.drugstore.com/summers-eve-deodorant-spray-baby-powder/qxp214451?catid=184079, 2 pages, printed on Mar. 23, 2009.
Product Description, "Zinc glycinate", Chem Blink, www.chemblink.com/products/14281-83-5.htm, 1 page, printed on Apr. 24, 2009.
Artiaga, F. "Facts on vaginal odor", Livestrong.com, www.livestrong.com/article/2773-facts-vaginal-odor/, pp. 1-3, (2011), printed on Aug. 16, 2012.
Pruthi, S. "Vaginal odor: What causes it?", MayoClinic.com, www.mayoclinic.com/health/vaginal-odor/AN00097, pp. 1-2, (2007), printed on Apr. 22, 2009.
"Queen Helene Deodorant Stick", EWG's Skin Deep® Cosmetics Database, found at http://www.ewg.org/skindeep/product/129714/Queen_Helene_Deodorant_Stick%2C_Tea_Tree_Oil_%28old_formulation%29/, pp. 1-3, updated Oct. 2009.
Parril, A., "Amino acid structures", Michigan State University Department of Chemistry, found at www.cem.msu.edu/-cem252/sp97/ch24/ch24aa.html, pp. 1-2, (Feb. 4, 1997).
Nordquist, c., "What is body odor (B.O.)? What causes body odor", Medical News Today, found at www.medicalnewstoday.com/printerfriendlynews.php?newsid=173478, pp. 1-6, (Dec. 9, 2009).

* cited by examiner

*Primary Examiner* — Shaojia Anna Jiang
*Assistant Examiner* — Michael C Henry
(74) *Attorney, Agent, or Firm* — Evan Law Group LLC

(57) ABSTRACT

A deodorant composition contains β-cyclodextrin, a fixative, a preservative, and a solvent.

10 Claims, No Drawings

DEODORANT COMPOSITIONS

CROSS REFERENCE TO RELATED APPLICATION

This application claims priority to provisional application No. 61/389,132 entitled "Deodorant Compositions" filed 1 Oct. 2010, the entire contents of which are hereby incorporated by reference, except where inconsistent with the present application.

BACKGROUND

Vaginal odor is a common problem for women around the world. Many attribute the unpleasant odor to lack of cleanliness. In actuality, the odor is caused by an imbalance in the bacteria within the vagina. Both "good" and "bad" bacteria naturally exist in the vaginal area. However, when the natural ratio of good to bad bacteria becomes imbalanced the result is an unpleasant odor. Vaginal odor can have a significant impact on the lives of those who suffer from it. The sometimes intense odor can adversely impact quality of life by causing those afflicted to shy away from both social and intimate contact. This can significantly affect the ability to construct and maintain healthy relationships.

SUMMARY

In a first aspect, the invention provides a deodorant composition comprising β-cyclodextrin, a fixative, a preservative, and a solvent.

In a second aspect, the invention provides a deodorant composition comprising β-cyclodextrin, hydroxyethylcellulose, phenoxyethanol, methylparaben, propylene glycol, polysorbate 20 and water.

In a third aspect, the invention provides a method of making a deodorant composition, comprising mixing ingredients comprising β-cyclodextrin, a fixative, a preservative, and a solvent.

In a fourth aspect, the invention provides deodorant compositions produced by a method comprising mixing ingredients comprising β-cyclodextrin, a fixative, a preservative, and a solvent.

In a fifth aspect, the invention provides a method of deodorizing skin, comprising applying a composition comprising β-cyclodextrin, a fixative, a preservative, and an emollient.

DETAILED DESCRIPTION

The present invention makes use of the discovery that β-cyclodextrin provides for improved deodorant compositions. Without being bound to any particular theory, it is believed that the β-cyclodextrin forms inclusion complexes with the chemicals responsible for malodor. Such volatile molecules are thereby trapped in the central cavity of the cyclodextrins, preventing their release in the atmosphere and the resulting malodor.

The deodorant composition of the invention includes a cyclodextrin. A "cyclodextrin" is defined as a compound of Formula 1:

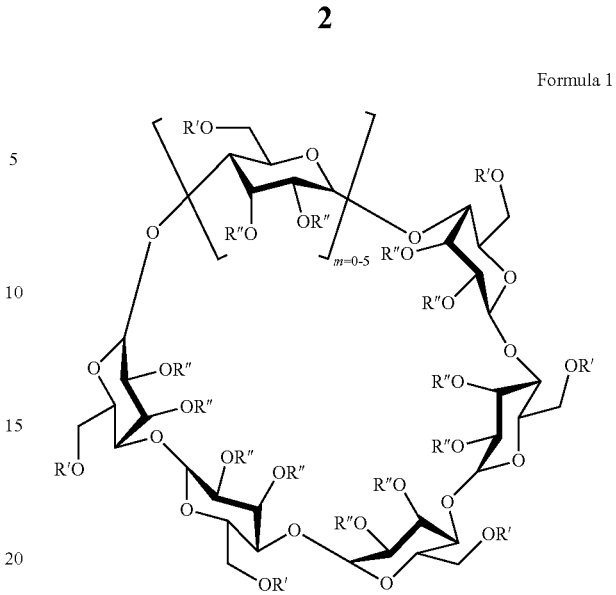

Formula 1

β-cyclodextrin, where n is equal to 2, is used in the compositions. Without being bound to any particular theory, it appears that the size of the central cavity of β-cyclodextrin is optimal for forming inclusion complexes with chemicals which cause malodor.

The R' and R" groups may independently be H, an alkyl and/or an ether group, such as —$CH_3$, —$CH_2CH_3$, —$CH_2OCH_3$, —$CH_2OCH_2CH_3$ and —$CH_2CH_2OCH_3$. Preferred cyclodextrins include those where all R' and R" groups are hydrogen atoms, or "natural cyclodextrins."

The deodorant composition preferably includes 0.01% (w/w) to 5% (w/w) of the cyclodextrin. More preferably, the composition comprises 0.05% (w/w) to 0.2% (w/w) of the cyclodextrin. Most preferably, the composition comprises 0.1% (w/w) to 0.2% (w/w) of the cyclodextrin. β-cyclodextrin present in amounts greater than 0.2% may not be stable with respect to precipitation. The term "(w/w)" is defined as the ratio of the weight of a component to the weight of the composition containing the component. Unless otherwise noted, all quantities are expressed in (w/w) percentages.

The composition may be in the form of a lotion, fluid, cream, gel stick, powder or spray. Preferably, the composition is in the form of a solution having a surface tension of less than 70 dyn/cm, more preferably less than 40 dyn/cm, for ease of use as a spray. The composition is preferably supplied in a spray bottle.

When the composition is in the form of a solution, aqueous solutions are preferred. Mixtures of water with water-miscible solvents, for instance alcohols such as methanol, ethanol, and propanol, are also acceptable.

A fragrance may be added to the composition in order to give it a pleasant odor. The quantity of fragrance is preferably 0.01% to 1%, more preferably 0.025% to 0.075%, most preferably 0.04% to 0.06%.

A fixative is also present in order to aid in maintaining the fragrance on the skin. Without being bound to any particular theory, it appears that the fixative forms a film on the skin and that the fragrance is released from the film slowly over time. Example fixatives include polyethylene glycol, polyacrilic acid, vegetable gum, hydroxymethylcellulose, hydroxyethylcellulose, and hydroxypropylcellulose. Hydroxyethylcellulose is a preferred fixative.

The amount of fixative is ideally sufficient to slow down fragrance release, but not so high as to cause the formation of a tacky, translucent or opaque solution. Preferably, the composition includes 1% to 6% of fixative, more preferably 2% to 5%, most preferably 3.5% to 4.5%.

Small quantities of a salt may be added to the composition. Without being bound to any particular theory, it appears that the salt improves the solubility of the fixative, yielding a homogeneous, clear solution. Preferred salt cations include $Na^+$ and $K^+$. Preferred salt anions include strong acid counterions such as $Cl^-$. The amount of salt in the composition is preferably 0.001% to 0.1%, more preferably 0.005% to 0.05%, most preferably 0.01% to 0.03%.

Preservatives, preferably chosen from those that do not fit in the central cavity of the β-cyclodextrin, may be added to the composition. Example preservatives include the parabens, such as methylparaben, ethylparaben, propylparaben, butylparaben, and their salts. Other preservatives include phenoxyethanol, methylisothiazoline, benzoic acid, 1,3-bis(hydroxymethyl)-5,5-dimethylimidazolidine-2,4-dione (also known as DMDM hydantoin), and sodium hydroxymethyl glycinate. Preferred preservatives include commercially available preservative blends, for example the NEOLONE™ family of preservatives (available from Rohm & Haas, Philadelphia, Pa.), such as NEOLONE™ MXP (a mixture including phenoxyethanol, methylparaben, propylparaben and methylisothiazolone). Other preservatives include Bronopol (2-bromo-2-nitropropane-1,3-diol) and Optiphen MIT Plus (a mixture of methylisothiazolinone, phenethyl alcohol and PPG-2-methyl ether), a combination of which provides preservation against the broadest group of microorganisms, when combined with EDTA at a pH of 5.1.

The composition preferably includes 0.01% to 1% of a preservative. The amount of preservative is more preferably 0.1% to 0.9%, most preferably 0.1% to 0.5%.

Surfactants may be added to the composition to increase the solubility of the cyclodextrin and/or other components. Surfactants that are routinely used in skin care products are preferred. Example surfactants include polysorbates, for example polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and polysorbate 80 (polyoxyethylene (20) sorbitan monooleate). Fatty acids, their ethoxylated derivatives, and their salts, for instance cocoamphocarboxyglycinate disodium and cocoamidopropyl oxide, provide additional classes of surfactants for the composition.

The composition preferably includes 0.01% to 3% of a surfactant. The amount of surfactant is more preferably 0.1% to 2%, most preferably 0.5% to 1.5%.

The pH of the composition is preferably 4.5 to 5.5. More preferably, the pH is 4.7 to 5.3, most preferably 4.9 to 5.1. A pH adjusting agent, for example an acid, base, or buffer, may be added to the composition to adjust the pH to desired values. Example pH adjusting agents include organic acids, mineral acids, ammonia, amines, and alkali metal and alkaline earth metal salts of weak acid anions such as carbonate, acetate, carbamate, citrate, glutamate, phosphate, polyphosphate, silicate, and borate.

Organic acids, and particularly carboxylic acids, are preferred pH adjusting agents. More preferred organic acids include those usually found in skin care products, notably α-hydroxy acids such as citric acid, lactic acid, glycolic acid, and mandelic acid.

Chelating agents may also be part of the composition, for example to prevent oxidation reactions catalyzed by metal ions such as $Mg^{2+}$ and $Ca^{2+}$. Example chelating agents include ethylenediaminetetraacetic acid (EDTA), ethylene glycol tetraacetic acid (EGTA), N,N'-ethylenediaminediacetic acid ($H_2$EDDA), 1,2-diaminocyclohexane-N,N,N',N'-tetraacetic acid ($H_4$CyDTA), 2,3-dimercapto-1-propanesulfonic acid (DMPS), dimercaptosuccinic acid (DMSA), diethylene triamine pentaacetic acid (DTPA), and crown ethers, as well as salts and complexes thereof.

The composition preferably includes 0.005% to 1% of a chelating agent. The amount of chelating agent is more preferably 0.01% to 0.5%, most preferably 0.03% to 0.08%. 0.05% EDTA is especially preferred.

Moisturizers, such as those commonly used in skin care products, may also be present in the composition. Example moisturizers include hyaluronic acid and its salts, sodium pyrrolidone carbonic acid (sodium PCA), and PEG-75 lanolin, (ethoxylated lanolin with a mean chain length of 75 ethylene oxide units).

When hyaluronic acid or one of its salts is added to the composition, it is preferably in amounts ranging from 0.05% to 2%, more preferably 0.1% to 1%, most preferably 0.15% to 0.3%. If sodium PCA is added, preferred amounts are from 0.1% to 2%, more preferably 0.5% to 1.5%, most preferably 0.8% to 1.2%. In the case PEG-75 lanolin is added, preferred amounts are 0.1% to 2%, more preferably 0.2% to 0.6%, most preferably 0.3% to 0.5%.

The composition may also contain emollients. Emollients routinely used in skin care are preferred, for example vegetable oils such as coconut oil, palm kernel oil, nut oil, mineral oils such as petroleum jelly, waxes such as carnauba wax and paraffin wax, and synthetic emollients such as silicon oil and propylene glycol. Propylene glycol is particularly preferred. The composition preferably includes 0.01% to 10% of an emollient. The amount of emollient is more preferably 0.1% to 2%, most preferably 0.2% to 0.8%.

Instructions may be optionally provided with the deodorant compositions of the invention. Instructions may include directions regarding how to apply the compositions to the human body. The instructions may be present in a variety of forms, including one or more printed sheets, printing on the outside or inside the exterior package, writing incorporated on one or more of the containers enclosed in the exterior package, a CD-ROM, a DVD-ROM, a uniform resource locator (URL) for a website, and the like.

The optional exterior package may be sized and configured to contain one or more other components of the composition. An exterior package may be a cup, a bottle, a vial, a tube, or the like, which may be formed in part or in whole from plastic, glass, paper, STYROFOAM®, and the like. A spray bottle is a preferred packaging for the composition.

The optional exterior package may include one or more supporting structures, such as walls, wells, movable or removable trays, etc., so as to segregate the various components of the composition. Supporting structures may be formed in part or in whole from plastic, glass, paper, STYROFOAM®, and the like.

EXAMPLE

The ingredients of a liquid deodorant composition comprising β-cyclodextrin were mixed in a vessel in the quantities shown below in the table. The composition is preferably applied to the body by means of a sprayer.

| Ingredient | Percentage (w/w) |
| --- | --- |
| Purified water | 91.733 |
| Propylene glycol | 0.5 |
| Hydroxyethylcellulose | 3.75 |

-continued

| Ingredient | Percentage (w/w) |
| --- | --- |
| Polysorbate 20 | 1 |
| Sodium hyaluronate | 0.25 |
| Sodium pyrrolidone carbonic acid | 1 |
| PEG-75 lanolin | 0.4 |
| Cococamphocarboxyglycinate | 0.132 |
| β-cyclodextrin | 0.15 |
| Cocoamidopropyl oxide | 0.113 |
| Bronopol | 0.075-0.1 |
| Optiphen MIT Plus | 0.075-0.15 |
| Fragrance | 0.05 |
| EDTA | 0.05 |
| Sodium chloride | 0.005 |
| Citric acid | 0.017 |

Three preservative levels studied passed a seven (7) day screening test. All three levels were equally effective, with the exception of 0.1% Bronopol with 0.075% Optiphen MIT Plus, which showed a lower efficacy (two log) against the *A. niger* mold. The table below shows the Log reduction in the microorganism specified after 7 days for the three preservative levels studied.

| | 0.1% Bronopol/0.075% Optiphen MIT Plus | 0.075% Bronopol/0.175% Optiphen MIT Plus | 0.075% Bronopol/0.15% Optiphen MIT Plus |
| --- | --- | --- | --- |
| *E. coli* | 6 | 6 | 6 |
| *P. aeruginosa* | 6 | 6 | 6 |
| *S. aureus* | 6 | 6 | 6 |
| *C. albicans* | 6 | 6 | 6 |
| *A. niger* | 5 | 7 | 7 |
| Pool | 6 | 6 | 6 |

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A deodorant composition consisting essentially of
   0.01% to 5% of β-cyclodextrin,
   3.5% to 4.5% of hydroxyethylcellulose,
   0.1% to 0.50% of 2-bromo-2-nitropropane-1,3-diol,
   0.1% to 0.50% of a mixture of methylisothiazolinone, phenethyl alcohol, and PPG-2-methyl ether,
   0.2% to 0.8% of propylene glycol,
   0.1% to 0.5% of polysorbate 20,
   0.03% to 0.08% of EDTA,
   a solvent,
   optionally a fragrance,
   optionally a pH adjusting agent,
   optionally a salt, and
   optionally a moisturizer
   wherein the composition is not translucent and is not opaque.

2. The composition of claim 1, wherein the β-cyclodextrin is present in an amount of 0.05% to 0.2%.

3. The composition of claim 1, wherein the β-cyclodextrin is present in an amount of 0.1% to 0.2%.

4. The composition of claim 1, wherein the solvent is selected from the group consisting of water, an alcohol, and mixtures thereof.

5. The composition of claim 1, wherein the solvent is water.

6. The composition of claim 1, containing the fragrance.

7. The composition of claim 1, containing the pH adjusting agent.

8. The composition of claim 1, containing the salt.

9. The composition of claim 1, containing the moisturizer.

10. The composition of claim 1, wherein the composition has a pH of from 4.5 to 5.5.

* * * * *